United States Patent
Schulz et al.

Patent Number: 6,054,407
Date of Patent: Apr. 25, 2000

[54] PEROXO-CONTAINING METAL COMPLEXES HAVING AMINE OXIDE, PHOSPHINE OXIDE, ARSINE OXIDE, PYRIDINE N-OXIDE OR PYRIDINE LIGANDS AS EPOXIDATION CATALYSTS

[75] Inventors: Michael Schulz; Joaquim Henrique Teles, both of Ludwigshafen; Jörg Sundermeyer, Sommerhausen; Günter Wahl, Würzburg, all of Germany

[73] Assignee: BASF Aktiengeslischaft, Ludwigshafen, Germany

[21] Appl. No.: 09/029,737

[22] PCT Filed: Sep. 4, 1996

[86] PCT No.: PCT/EP96/03888

§ 371 Date: Mar. 11, 1998

§ 102(e) Date: Mar. 11, 1998

[87] PCT Pub. No.: WO97/10054

PCT Pub. Date: Mar. 20, 1997

[30] Foreign Application Priority Data

Sep. 11, 1995 [DE] Germany .................. 195 33 331

[51] Int. Cl.⁷ .............. B01J 31/32; B01J 31/34; B01J 31/36; B01J 31/38; C07D 301/12

[52] U.S. Cl. ............ 502/155; 502/164; 502/210; 549/531

[58] Field of Search ............ 549/531; 502/155, 502/164, 210

[56] References Cited

U.S. PATENT DOCUMENTS

| | | |
|---|---|---|
| 3,953,362 | 4/1976 | Lines et al. |
| 4,104,312 | 8/1978 | Angstadt et al. |
| 4,973,718 | 11/1990 | Buchler et al. ......... 549/531 |
| 5,223,631 | 6/1993 | Cheng et al. |

FOREIGN PATENT DOCUMENTS

| | | |
|---|---|---|
| 0 097 551 | 5/1983 | European Pat. Off. |
| 0 215 415 | 12/1991 | European Pat. Off. |
| 2 489 710 | 3/1982 | France. |
| WO 96 20788 | 7/1996 | WIPO. |

OTHER PUBLICATIONS

M. Postel et al ; Structural and Stereodynamics . . . ; Inorganic Chimica Acta vol. 32 pp. 175–180, May 11, 1978.
Chem. Abstract 70:110163 RN–23303–41–5.
Chem. Abstract 84:173189.
Chem Abstract 83:137726.

*Primary Examiner*—Alan L. Rotman
*Assistant Examiner*—Rita Desai
*Attorney, Agent, or Firm*—Oblon, Spivak, McClelland, Maier & Neustadt, P.C.

[57] ABSTRACT

Olefins can be epoxidized using catalysts I

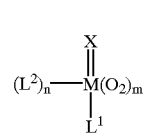

(I)

where
M is a metal of the 4th to 7th transition group of the Periodic Table of the Elements,
$L^1$ is an amine oxide, phosphine oxide, arsine oxide, pyridine N-oxide or pyridine ligand of the formula II, III, VII or VIII,
$L^2$ is a customary auxiliary ligand or a further ligand $L^1$ or a free coordination site,
X is oxo oxygen or an imido ligand,
m is 1 or 2, and
n is 1, 2 or 3.

10 Claims, No Drawings

PEROXO-CONTAINING METAL COMPLEXES HAVING AMINE OXIDE, PHOSPHINE OXIDE, ARSINE OXIDE, PYRIDINE N-OXIDE OR PYRIDINE LIGANDS AS EPOXIDATION CATALYSTS

CROSS-REFERENCE

This application is a 371 of PCT/EP96/03888 filed Sep. 4, 1996.

BACKGROUND OF THE INVENTION

The present invention relates to novel catalysts in the form of peroxo-containing metal complexes having amine oxide, phosphine oxide, arsine oxide, pyridine N-oxide or pyridine ligands, which catalysts are suitable for the epoxidation of olefins using aqueous hydrogen peroxide. Furthermore, the invention relates to a process for preparing these catalysts and a corresponding epoxidation process.

DESCRIPTION OF THE BACKGROUND

The epoxidation of olefins using aqueous hydrogen peroxide ($H_2O_2$) is only successful in the presence of organic or inorganic activators or catalysts. The transfer of the oxygen atom from $H_2O_2$ to the substrate can occur in a stoichiometric or catalytic reaction. However, in the case of the use of hydrogen peroxide, the disadvantage of the necessity of an activator or catalyst is more than compensated for by the ecological potential of hydrogen peroxide. In contrast to other oxidates, oxidation using $H_2O_2$ gives only water as by-product. A further advantage is the high active oxygen content of hydrogen peroxide which, at 47%, is far above that of all other customary oxidates (except for $O_2$).

Hydrogen peroxide has hitherto been used industrially mainly as an unselective oxidizing agent, for example for the bleaching of paper, textiles and cellulose or in wastewater treatment. A significant proportion of the world production of $H_2O_2$ goes into the manufacture of inorganic peroxo compounds for detergents. Only about 10% are used for the preparation of organic chemicals such as percarboxylic acids or N-oxides, which is attributed not least to the lack of suitable selective activators or catalysts.

One of the most common methods for the stoichiometric activation of hydrogen peroxide is the reaction with carboxylic acids to give percarboxylic acids which can epoxidize a variety of olefins. However, a problem here is the acid-sensitivity of many epoxides, particularly in aqueous medium, and also the liability of the percarboxylic acids which leads to losses in yield.

Peroxo-containing transition metal complexes such as $MO(O_2)_2L_2$ (M=Mo or W, L=$H_2O$, DMF (dimethylformamide) or HMPA (hexamethylphosphoramide)), which can easily be prepared from $H_2O_2$ and the corresponding metal oxide $MO_3$ are also able to epoxidize olefins, which corresponds to a stoichiometric activation of $H_2O_2$. Compounds of this specific type have the advantage of being readily available.

For catalytic activation in the epoxidation of olefins using $H_2O_2$, use is made, for example, of catalysts derived from the above-mentioned peroxo-containing transition metal complexes $MO(O_2)_2L_2$. Thus, U.S. Pat. No. 3,953,362 (1) describes molybdenum complexes obtainable from $MoO_3$, $H_2O_2$ and tertiary amines whose three organic radicals are each $C_1$–$C_{10}$-alkyl or $C_6$–$C_{10}$-aryl groups, or the N-oxides of such tertiary amines, as catalysts for epoxidations using $H_2O_2$.

EP-A 215 415 (2) relates to an oxidation process for converting olefins into aldehydes or ketones by means of oxodiperoxomolybdenum or tungsten complexes having phosphoramide and, inter alia, also amine oxide or phosphine oxide ligands. Examples of amine oxides mentioned are pyridine N-oxide, 4-picoline N-oxide, trioctylamine N-oxide and phenylpropylpyridine N-oxide; trimethylphosphine oxide is mentioned as an example of a phosphine oxide.

EP-A 097 551 (3) discloses the use of vanadium, niobium or tantalum complexes of the formula $MO(O_2)_2L_2$ having phosphoramide and also amine oxide or phosphine oxide ligands as epoxidation catalysts for olefins. Examples of amine oxides which are mentioned are trimethylamine N-oxide, N-methylmorpholine N-oxide, pyridine N-oxide, 2-, 3- or 4-picoline N-oxide, quinoline N-oxide and 2,2'-bipyridine N-oxide; examples of phosphine oxides which are mentioned are triphenylphosphine oxide, trimethylphosphine oxide, methyldiphenylphosphine oxide, diethylphenylphosphine oxide and trimorpholinophosphine oxide.

However, disadvantages of the complexes described in the documents (1) to (3) are the comparatively low activities, epoxide selectivities and olefin conversions in the case of olefin epoxidations using aqueous $H_2O_2$.

SUMMARY OF THE INVENTION

It is an object of the present invention to provide metal complex catalysts, in particular for olefin epoxidations using aqueous $H_2O_2$, which are simple and economical to prepare and also have a high effectiveness and efficiency.

DETAILED DESCRIPTION OF THE INVENTION

We have found that this object is achieved by catalysts of the general formula I

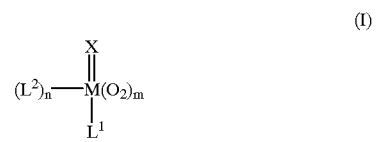

(I)

where

M is a metal from the 4th to 7th transition group of the Periodic Table of the Elements, $L^1$ is an amine oxide ligand of the formula II, a phosphine oxide or arsine oxide ligand of the formula III, a pyridine N-oxide ligand of the formula VII or a pyridine ligand of the formula VIII

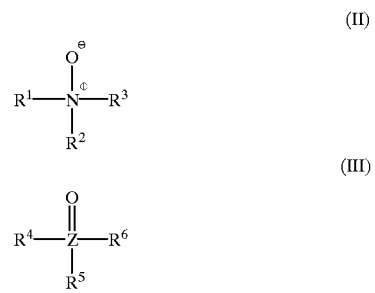

-continued

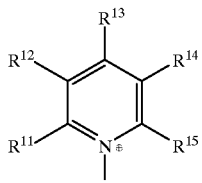
(VII)

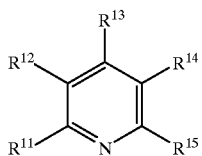
(VIII)

where

R¹ to R³ are identical or different $C_1$–$C_{30}$-alkyl, $C_7$–$C_{30}$-aralkyl or $C_6$–$C_{30}$-aryl radicals which can additionally contain ether oxygen atoms, carbonyl groups, hydroxyl groups, alkoxy groups, carboxyl groups, cyano groups, carboxylic ester groups, sulfo groups, phosphonic acid groups, nitro groups, halogen atoms and/or unsubstituted or $C_1$–$C_4$-alkyl-substituted amino groups as functional groups, where at least one of the radicals R¹ to R³ has to have at least 11 carbon atoms and the two other radicals can be linked to form a ring, and R⁴ to R⁶ are identical or different $C_4$–$C_{30}$-alkyl, $C_7$–$C_{30}$-aralkyl or $C_{10}$–$C_{30}$-aryl radicals which can additionally contain ether oxygen atoms, carbonyl groups, hydroxyl groups, alkoxy groups, carboxyl groups, cyano groups, carboxylic ester groups, sulfo groups, phosphonic acid groups, nitro groups, halogen atoms and/or unsubstituted or $C_1$–$C_4$-alkyl-substituted amino groups as functional groups, and R¹¹ to R¹⁵ are, independently of one another, hydrogen or identical or different $C_1$–$C_{30}$-alkyl radicals, $C_7$–$C_{30}$-aralkyl radicals, $C_6$–$C_{30}$-aryl radicals, $C_7$–$C_{30}$-alkoxy groups, $C_7$–$C_{30}$-aralkoxy groups, $C_6$–$C_{30}$-arlyoxy groups or dihydrocarbylamino groups having identical or different $C_1$–$C_{30}$-alkyl radicals, $C_7$–$C_{30}$-aralkyl radicals and/or $C_6$–$C_{30}$-aryl radicals as hydrocarbyl radicals which can additionally contain ethyloxygen atoms, carbonyl groups, hydroxyl groups, alkoxy groups, carboxyl groups, cyano groups, carboxylic ester groups, sulfo groups, phosphonic acid groups, nitro groups, halogen atoms and/or unsubstituted or $C_1$–$C_4$-alkyl-substituted amino groups as functional groups, where at least one of the radicals R¹¹ or R¹⁵ has to be hydrogen, the sum of the carbon atoms in the radicals R¹¹ to R¹⁵ has to be at least 8 and the radicals R¹¹ to R¹⁵ can be linked in pairs to form rings, L² is an auxiliary ligand selected from the group consisting of oxo, halides, pseudohalides, carboxylates, phenoxides, alkoxides, enolates, ketones, ethers, amines, amides, urea, urea derivatives and water or a further ligand L¹ or a free coordination site, X is oxo oxygen or an unsubstituted or $C_1$–$C_4$-alkyl-substituted imido ligand, Z is phosphorus or arsenic, m is 1 or 2 and n is 1, 2 or 3.

The catalysts I of the present invention differ from those known from the prior art in that they have longer-chain or bulkier radicals in the ligands L¹ than is the case in the amine oxide or phosphine oxide systems previously described for this purpose. In the case of the amine oxide ligands II, at least one of the three radicals R¹ to R³ has to contain at least 11, preferably at least 12, in particular at least 14, carbon atoms. This radical is preferably a linear or branched alkyl group. In the case of the phosphine oxide or arsine oxide ligands III, the lower limit for the size of linear or branched alkyl radicals R⁴ to R⁶ is 4, preferably 6, in particular 8, carbon atoms, the lower limit for the size of aralkyl radicals R⁴ to R⁶ is 7, preferably 9, in particular 12, carbon atoms, and the lower limit for the size of aryl radicals R⁴ to R⁶ is 10, preferably 12, in particular 14, carbon atoms. For the pyridine N-oxide and pyridine ligands VII or VIII, the sum of the carbon atoms of the ring substituents has to be at least 8, preferably at least 9; in particular, one of the radicals R¹¹ to R¹⁵ is a long-chain linear or branched alkyl radical having at least 8, especially at least 9, carbon atoms.

Suitable transition metals for the catalyst complexes of the present invention are, in particular, titanium, zirconium, hafnium, vanadium, niobium, tantalum, chromium, molybdenum, tungsten, manganese and rhenium. Particular preference is given to molybdenum and tungsten.

Typical examples of amine N-oxide ligands II are:
dimethyl-n-undecylamine oxide,
dimethyl-n-dodecylamine oxide,
dimethyl-n-tetradecylamine oxide,
dimethyl-n-hexadecylamine oxide,
dimethyl-n-octadecylamine oxide,
dimethyl-n-eicosylamine oxide,
methyldi(n-dodecyl)amine oxide,
methyldi(n-octadecyl)amine oxide,
tri(n-dodecyl)amine oxide,
tri(n-octadecyl)amine oxide,
benzyldi(n-dodecyl)amine oxide,
diphenyl-n-octadecylamine oxide,
N-undecylmorpholine oxide,
N-dodecylpiperidine oxide,
dimethyl(6-phenylhexyl)amine oxide,
dimethylbisphenylamine oxide and
methyl-n-dodecyl(6-phenylhexyl)amine oxide.

Typical examples of phosphine oxide and arsine oxide ligands III are:
tri-n-butylphosphine oxide and tri-n-butylarsine oxide,
tri-tert-butylphosphine oxide and tri-tert-butylarsine oxide,
tri-n-hexylphosphine oxide and tri-n-hexylarsine oxide,
tri-n-octylphosphine oxide and tri-n-octylarsine oxide,
tri(2-ethylhexyl)phosphine oxide and tri(2-ethylhexyl)arsine oxide,
tri-n-dodecylphosphine oxide and tri-n-dodecylarsine oxide,
tri-n-octadecylphosphine oxide and tri-n-octadecylarsine oxide,
di-n-butyl-n-octylphosphine oxide and di-n-butyl-n-octylarsine oxide,
n-butyldi-n-octylphosphine oxide and n-butyldi-n-octylarsine oxide,
tribenzylphosphine oxide and tribenzylarsine oxide,
benzyldi-n-octylphosphine oxide and benzyldi-n-octylarsine oxide,
naphthyldi-n-octylphosphine oxide and naphthyldi-n-octylarsine oxide and
di-n-butylnaphthylphosphine oxide and di-n-butylnaphthylarsine oxide.

Typical examples of pyridine N-oxide and pyridine ligands VII and VIII are:
4-(1-octyl)pyridine and the corresponding N-oxide,
4-[1-(2-ethylhexyl)]pyridine and the corresponding N-oxide,
4-(1-nonyl)pyridine and the corresponding N-oxide, 4-(5-nonyl)pyridine and the corresponding N-oxide,
4-(1-decyl)pyridine and the corresponding N-oxide,
4-(1-dodecyl)pyridine and the corresponding N-oxide,
4-(n-octoxy)pyridine and the corresponding N-oxide,
4-(2-ethylhexoxy)pyridine and the corresponding N-oxide,
4-(n-nonoxy)pyridine and the corresponding N-oxide,
4-(di-n-octylamino)pyridine and the corresponding N-oxide and
4-(di-2-ethylhexylamino)pyridine and the corresponding N-oxide.

If the radicals $R^1$ to $R^6$ and $R^{11}$ to $R^{15}$ contain additional ether oxygen atoms, then such radicals are derived, in particular, from corresponding ethylene oxide, propylene oxide, butylene oxide or tetrahydrofuran reaction products.

Alkoxy substituents and carboxylic ester substituents on $R^1$ to $R^6$ and $R^{11}$ to $R^{15}$ preferably bear $C_1$–$C_4$-alkyl radicals, in particular methyl or ethyl. Halogen atoms on $R^1$ to $R^6$ and $R^{11}$ to $R^{15}$ are, in particular, chlorine or bromine. The number of the listed functional groups on $R^1$ to $R^6$ and $R^{11}$ to $R^{15}$ is, if any are present, usually from 1 to 3, in the case of ether oxygen atoms from 1 to 14, depending on chain length.

The auxiliary ligands $L^2$ are those which are customarily used and with which those skilled in the art are therefore familiar.

Preferred catalysts of the present invention are those of the general formula Ia or Ib

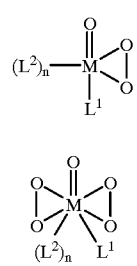

(Ia)

(Ib)

where $L^2$ is water and the variables M, $L^1$ and n are as defined above.

In the case of M=chromium, molybdenum or tungsten, the number n of the ligands $L^2$ is preferably 1.

A preferred embodiment comprises catalysts of the present invention I or Ia or Ib in which $L^1$ is an amine oxide ligand II bearing $C_1$–$C_{20}$ alkyl groups as radicals $R^1$ to $R^3$, where at least one of the radicals $R^1$ to $R^3$ has to be a $C_{12}$–$C_{20}$-alkyl group and the two other radicals can be linked to form a saturated 5- or 6-membered ring which can contain further hetero atoms selected from the group consisting of oxygen and nitrogen.

A further preferred embodiment comprises catalysts of the present invention I or Ia or Ib in which $L^1$ is a phosphine oxide or arsine oxide ligand III bearing $C_4$–$C_{20}$-alkyl groups as radicals $R^4$ to $R^6$.

The catalyst complexes I of the present invention are advantageously prepared from another complex of the metal M and hydrogen peroxide.

The complexes I are usually obtained by replacing the ligands L in the abovementioned peroxo-containing transition metal complexes $MX(O_2)_m(L^2)_{n+1}$, where M, X, m and n are as defined above and L is, in particular, $H_2O$, DMF or HMPA, by amine oxides II or phosphine oxides III. These precursor complexes themselves can usually be prepared very simply from inexpensive starting materials (metal oxide, $H_2O_2$ and ligand or ligand precursor).

Advantageously, the catalysts I are prepared in situ either by dissolving metal oxides in an excess of aqueous $H_2O_2$ or from readily available precursors such as $MO_2Cl_2$(dme) (dme=dimethoxyethane), and activation by adding the necessary amount of amine oxide II, phosphine or arsine oxide III, pyridine N-oxide VII or pyridine VIII. In place of the amine N-oxides or phosphine or arsine oxides, it is also possible to directly add the corresponding amines or phosphines or arsines, since they are oxidized in situ by $H_2O_2$ to give the desired amine N-oxides or phosphine oxides. The catalysts can be generated in situ or can also be prepared separately, isolated and characterized.

Other suitable precursors for the catalyst complexes I of the present invention are complexes of the formula VI

(VI)

where

Y is halide, eg. chloride, or pseudohalide, eg. thiocyanate, and the variables M, X, $L^1$, $L^2$ and n are as defined above. The complexes VI are easily converted into the complexes I in the presence of $H_2O_2$.

The catalysts I of the present invention are very suitable for the catalytic activation of oxidation reactions, in particular for the epoxidation of olefins, especially using aqueous hydrogen peroxide as epoxidizing agent.

Accordingly, the present invention also provides a process for preparing epoxides of the general formula IV

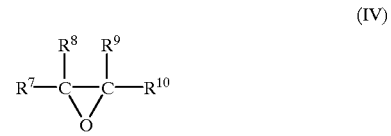

(IV)

where $R^7$ to $R^{10}$ are identical or different and are hydrogen or unsubstituted or substituted alkyl, alkenyl, heteroalkyl, cycloalkyl, aryl or heteroaryl radicals, where the radicals $R^7$ to $R^{10}$ can also be linked to form rings, or substituents based on elements of the 4th to 7th main group of the Periodic Table of the Elements, from olefins of the general formula V

(V)

using aqueous hydrogen peroxide, wherein the epoxidation of the olefins V is carried out in the presence of the catalysts I of the present invention.

For the olefins which can be used, there is no restriction in respect of the type and number of substituents. Typical examples of olefins which can be epoxidized by the process of the present invention are ethylene, propene, 1-butene, 2-butene, isobutene, 1,3-butadiene, 1-pentene, 2-pentene, isoprene, cyclopentene, 1-hexene, cyclohexene, $C_8$–$C_{24}$-α-monoolefins, styrene, indene, norbornene, cyclopentadiene, dicyclopentadiene and also alkene oligomers having reactive double bonds, eg. polypropene and polyisobutene.

The olefins v can also bear substituents based on elements of the 4th to 7th main group on the olefinic double bond. Examples are vinylsilicones, vinylamines, vinylphosphines, vinyl ethers, vinyl sulfides and halogenated alkenes such as vinyl chloride, vinylidene chloride or trichloroethylene.

To carry out the epoxidation according to the present invention, it is usual to initially charge the catalyst I and to add the necessary amount of aqueous $H_2O_2$ and olefin, if desired dissolved in a suitable inert organic solvent. The concentration range of the aqueous $H_2O_2$ can be from 2 to 70% by weight, in particular from 5 to 50% by weight. Suitable inert organic solvents are, for example, chloroform, dichloromethane, ethers, carboxylic esters or aromatics. This usually gives a two-phase reaction mixture. When solvents miscible with water, for example methanol, acetone, dimethoxyethane or dioxane, are used, the reaction can also be carried out homogeneously.

The reaction conditions of the epoxidation according to the present invention are very mild, which is an advantage because of the high reactivity of the epoxides formed. Typically, the reaction is carried out at from −20 to 160° C., in particular from 20 to 100° C., especially from 50 to 80° C., ie. in a temperature range which is likewise favorable for removing the heat of reaction. Increased pressure is necessary only in the case of highly volatile olefins such as propene or butene; the reaction is normally carried out at atmospheric pressure.

Use of the ligands II, III, VII or VIII having lipophilic substituents in the form of long-chain or bulky radicals generally gives interphase-active catalysts so that the epoxidation can also advantageously be carried out in a two-phase system, ie. in two liquid phases which are not completely miscible with one another. This procedure has the advantage that, on the one hand, lipophilic, water-insoluble olefins can also be oxidized and that, on the other hand, the epoxides formed remain in the organic phase and the formation of undesired by-products is thus suppressed. In addition, the separation of the product is made easier by the two-phase procedure.

In a preferred embodiment, propene is epoxidized to propylene oxide by the process of the present invention, in particular in a two-phase system.

In a further preferred embodiment, 1,3-butadiene is epoxidized to vinyloxirane by the process of the present invention, in particular in a two-phase system.

Using the highly active catalysts I of the present invention, epoxides are obtained with high selectivities and at high conversion rates from olefins by means of aqueous hydrogen peroxide in a simple and economical procedure under mild and gentle conditions.

EXAMPLES

Example 1

Preparation of the catalyst stock solutions a) Preparation of an aqueous stock solution of $[Mo(O)(O_2)(H_2O)_2]$ 6.00 g (41.7 mmol) of $[MoO_3]$ were suspended with vigorous stirring in 24.0 g (212 mmol) of 30% strength by weight $H_2O_2$ solution. The colorless suspension was stirred for 4 hours at 40° C., forming a clear, light yellow solution which was stored at 4° C. $[Mo(O)(02)(H_2O)_2]$ content 1.39 mmol/g.

b) Preparation of an aqueous stock solution of $[W(O)(O_2)(H_2O)_2]$ 8.00 g (32.0 mmol) of $[WO_3.H_2O]$ were suspended with vigorous stirring in 24.0 g (212 mmol) of 30% strength by weight $H_2O_2$ solution. The yellow suspension was stirred for 6 hours at 40° C., forming a milky, turbid solution. After removal of the insoluble residue (25 mg) by centrifugation, the clear, colorless solution was stored at 4° C. $[W(O)(02)(H_2O)_2]$ content: 1.01 mmol/g.

Example 2

Preparation of the catalysts $[M(O)(O_2)_2L^1]$ a) Preparation of $[Mo(O)(O_2)_2\{OP(n\text{-}Oct)_3\}]$ 4 ml of tetrahydrofuran (THF) were first added to 1.86 g (2.58 mmol) of Mo stock solution (Example 1a). While stirring, 500 mg (1.29 mmol) of tri-n-octylphosphine oxide $[OP(n\text{-}Oct)_3]$ were added at 25° C. After vigorous stirring for 2 hours, the yellow solution was evaporated under reduced pressure to about 3 ml, with a yellow oil separating out. The reaction mixture was extracted with $CH_2Cl_2$ (3 times, 5 ml each time). The combined extracts were completely evaporated under reduced pressure. The light yellow, waxy residue was washed with water (2 times, 2 ml each time) and dried for 6 hours at 25° C./$10^{-5}$ mbar.

Yield: 675 mg (93%) of light yellow wax

DTA: 81° C. (exothermic decomposition)

CHN analysis: $C_{24}H_{51}PO_6Mo$ (562.6) calc. C, 51.24; H, 9.14; found C, 51.68; H, 9.45.

b) Preparation of $[W(O)(O_2)_2\{OP(n\text{-}Oct)_3\}]$ 12 ml of THF were first added to 6.00 g (6.06 mmol) of W stock solution (Example 1b). While stirring, 1.50 g (3.87 mmol) of $[OP(n\text{-}Oct)_3]$ were added to the solution at 25° C. After vigorous stirring for 4 hours, the colorless solution was evaporated under reduced pressure to about 5 ml, with a colorless oil separating out. The reaction mixture was extracted with $CH_2Cl_2$ (3 times, 10 ml each time). The combined extracts were completely evaporated under reduced pressure.

The colorless, oily residue was washed with water (3 times, 15 ml each time) and dried for 6 hours at 25° C./$10^{-5}$ mbar.

Yield: 2.40 g (95%) of colorless oil

DTA: 98° C. (exothermic decomposition)

CHN analysis: $C_{24}H_{51}PO_6W$ (650.0) calc. C, 44.35; H, 7.91; found C, 45.14; H, 8.53.

c) Preparation of $[Mo(O)(O_2)_2\{ONMe_2(n\text{-}C_{18}H_{37})\}]$ 6.00 g (5.74 mmol) of dimethyl-n-octadecylamine oxide $[ONMe_2(n\text{-}C_{18}H_{37})]$ (30% by weight in water) were added at 25° C. while stirring to 5.00 g (6.95 mmol) of Mo stock solution (Example 1a), with a pale yellow precipitate being spontaneously formed. After vigorous stirring for 2 hours, the precipitate was filtered off, washed with water (3 times, 50 ml each time) and dried under reduced pressure for 6 hours at 25° C./$10^{-5}$ mbar.

Yield: 2.00 g (71%) of pale yellow, amorphous solid

DTA: 78° C. (exothermic decomposition)

CHN analysis: $C_{20}H_{43}MoNO_6$ (489.5) calc. C, 49.07; H, 8.85; N, 2.86; found C, 49.07; H, 8.88; N, 2.82.

d) Preparation of $[Mo(O)(O_2)_2\{ON(dodec)_3\}]$ 1.20 g (2.23 mmol) of tri-n-dodecylamine oxide $[ON(dodec)_3]$ dissolved in 5 ml of $CH_2Cl_2$ were added at 25° C. while stirring to 2.00 g (2.87 mmol) of Mo stock solution (Example 1a). After vigorous stirring for 5 hours at 25° C., the organic phase was separated off, washed with water (3 times, 5 ml each time) and completely evaporated under reduced pressure. The pale yellow, amorphous residue was dried for 6 hours at 25° C./$10^{-5}$ mbar.

Yield: 2.81 g (95%) of pale yellow, amorphous solid

DTA: 75° C. (exothermic decomposition)

CHN analysis: $C_{36}H_{75}MoNO_6$ (713.9) calc. C, 60.57; H, 10.59; N, 1.96; found C, 60.62; H, 10.72; N, 1.95.

d) Preparation of $[W(O)(O_2)_2\{ON(dodec)_3\}]$ 1.30 g (2.42 mmol) of $[ON(dodec)_3]$ dissolved in 5 ml of $CH_2CL_2$ were added at 25° C. while stirring to 3.00 g (3.03 mmol) of W stock solution (Example 1b). After vigorous stirring for 5 hours at 25 °C, the organic phase was separated off, washed with water (3 times, 5 ml each time) and completely evaporated under reduced pressure. The colorless, sticky residue was dried for 6 hours at 25° C./$10^{-5}$ mbar.

Yield: 1.84 g (95%) of colorless, sticky wax

DTA: 68° C. (exothermic decomposition)

CHN analysis: $C_{36}H_{75}WNO_6$ (801.8) calc. C, 53.93; H, 9.43; N, 1.75; found C, 53.88; H, 9.29; N, 1.67.

Example 3

Catalytic oxidation of cyclooctene and 1-octene by 30% strength by weight $H_2O_2$ using catalysts of the type $MO(O_2)_2 L^1(H_2O)$ generated in situ 36 mmol of 30% strength by weight $H_2O_2$ and 9 mmol of olefin were added at 25° C. to an aliquot (0.36 mmol=4 mol %) of the catalyst stock solution described in Example 1. The reaction solution was subsequently admixed with 0.36 mmol of phosphine oxide or amine N-oxide ligand dissolved in 4 ml of $CHCl_3$ and stirred for 24 hours at 60° C. The olefin conversion and the epoxide selectivity were determined by gas chromatography.

The results of the experiments are summarized in Table 1.

The same results are also obtained in principle using the analogous, separately prepared catalysts described under Example 2 (in each case using 0.36 mmol dissolved in 4 ml of $CHCl_3$).

Examples 6 and 7

Epoxidation using $L^1$=4-(5-nonyl)pyridine

A glass autoclave was charged with 1-octene (500 mg, 4.45 mmol), $MO_3$ (0.17 mmol, 4.0 mol % based on 1-octene, as a 0.5 M solution in 30% strength by weight $H_2O_2$) and 4-(5-nonyl)pyridine (0.17 mmol dissolved in 3 ml of chloroform). $H_2O_2$ (17.8 mmol, as 30% strength by weight aqueous solution) was then added and the mixture was stirred at 60° C. Octene epoxide was the only product attempted. The octene oxide yields at various reaction times are summarized in Table 3.

TABLE 3

| | | Yield A of octene oxide (%) | |
|---|---|---|---|
| Example | $MO_3$ | A after t = 4 h | A after t = 24 h |
| 6 | $MoO_3$ | 7 | 23 |
| 7 | $WO_3$ | 7 | 11 |

Examples 8 and 9

Epoxidation using $L^1$=4-(5-nonyl)pyridine N-oxide

A glass autoclave was charged with 1-octene (500 mg, 4.45 mmol), $MO_3$ (0.17 mmol, 4.0 mol % based on 1-octene, as a 0.5 M solution in 30% strength by weight $H_2O_2$) and 4-(5-nonyl)pyridine N-oxide (0.17 mmol dissolved in 3 ml of chloroform). $H_2O_2$ (17.8 mmol, as 30% strength by

TABLE 1

| Olefin | Catalyst | Ligand $L^1$ | Olefin conversion (mol %) | Epoxide selectivity (mol %) | Remarks |
|---|---|---|---|---|---|
| Cyclooctene | $MoO(O_2)_2L^1(H_2O)$ | $H_2O$ | 2 | | for comparison |
| | | $OP(NMe_2)_3$ | 30 | | for comparison |
| | | $OP(t-Bu)_3$ | 85 | >98 | |
| | | $OP(n-C_8H_{17})_3$ | 100 | >98 | after 20 h |
| | | $ONMe_2(n-C_{18}H_{37})$ | 100 | >98 | after 3 h |
| | | $ON(n-C_{12}H_{25})_3$ | 100 | 95 | after 2 h |
| | $WO(O_2)_2L^1(H_2O)$ | $OP(n-C_8H_{17})_3$ | 36 | >98 | |
| | | $ONMe_2(n-C_{18}H_{37})$ | 98 | >98 | |
| 1-Octene | $MoO(O_2)_2L^1(H_2O)$ | $OP(n-C_8H_{17})_3$ | 46 | 97 | 15 equivalents of $L^1$ |
| | | $ONMe_2(n-C_{18}H_{37})$ | 63 | >98 | |
| | | $ON(n-C_{12}H_{25})_3$ | 91 | >98 | |

Examples 4 and 5

Epoxidation using $L^1$ =tri(n-dodecyl)arsine oxide

A glass autoclave was charged with 1-octene (500 mg, 4.45 mmol), $MO_3$ (0.17 mmol, 4.0 mol % based on 1-octene, as a 0.5 M solution in 30% strength by weight $H_2O_2$) and tri-(n-dodecyl)arsine oxide (0.17 mmol dissolved in 3 ml of chloroform). $H_2O_2$ (17.8 mmol, as 30% strength by weight aqueous solution) was then added and the mixture was stirred at 60° C. Octene epoxide was the only product attempted. The octene oxide yields at various reaction times are summarized in Table 2.

TABLE 2

| | | Yield A of octene oxide (%) | | |
|---|---|---|---|---|
| Example | $MO_3$ | A after t = 4 h | A after t = 24 h | A after t = 48 h |
| 4 | $MoO_3$ | 26 | 71 | 90 |
| 5 | $WO_3$ | 37 | 42 | 40 | weight aqueous solution) was then added and the mixture was stirred at 60° C. Octene epoxide was the only product attempted. The octene oxide yields at various reaction times are summarized in Table 4.

TABLE 4

| | | Yield A of octene oxide (%) | |
|---|---|---|---|
| Example | $MO_3$ | A after t = 4 h | A after t = 24 h |
| 8 | $MoO_3$ | 7 | 12 |
| 9 | $WO_3$ | 3 | 6 |

Examples 10 and 11

Epoxidation using $L^1$=4-(dioctylamino)pyridine

A glass autoclave was charged with 1-octene (500 mg, 4.45 mmol), $MO_3$ (0.17 mmol, 4.0 mol % based on 1-octene, as a 0.5 M solution in 30% strength by weight $H_2O_2$) and 4-(dioctylamino)pyridine (0.17 mmol dissolved in 3 ml of chloroform). $H_2O_2$ (17.8 mmol, as 30% strength by weight aqueous solution) was then added and the mixture was stirred at 60° C. Octene epoxide was the only product attempted. The octene oxide yields at various reaction times are summarized in Table 5.

TABLE 5

| | | Yield A of octene oxide (%) | | |
|---|---|---|---|---|
| Example | $MO_3$ | A after t = 4 h | A after t = 24 h | A after t = 48 h |
| 10 | $MoO_3$ | 24 | 32 | 37 |
| 11 | $WO_3$ | 11 | 16 | 16 |

We claim:

1. A catalyst of the general formula I

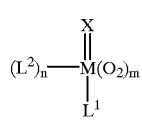

(I)

where
M is a metal selected from the group consisting of titanium, zirconium, hafnium, vanadium, niobium, tantalum, chromium, molybdenum, tungsten, manganese and rhenium, $L^1$ is an amine oxide ligand of the formula II, a phosphine oxide or arsine oxide ligand of the formula III, a pyridine N-oxide ligand of the formula VII or a pyridine ligand of the formula VIII

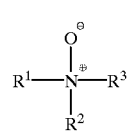

(II)

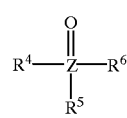

(III)

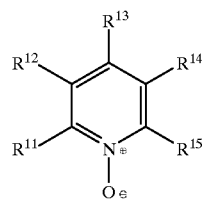

(VII)

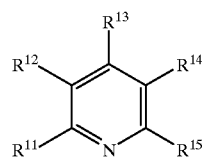

(VIII)

where
$R^1$ to $R^3$ are identical or different $C_1$–$C_{30}$-alkyl, $C_7$–$C_{30}$-aralkyl or $C_6$–$C_{30}$-aryl radicals which optionally contain ether oxygen atoms, carbonyl groups, hydroxyl groups, alkoxy groups, carboxyl groups, cyano groups, carboxylic ester groups, sulfo groups, phosphonic acid groups, nitro groups, halogen atoms and/or unsubstituted or $C_1$–$C_4$-alkyl-substituted amino groups as functional groups, where at least one of the radicals $R^1$ to $R^3$ has to have at least 11 carbon atoms and the two other radicals can be linked to form a ring, and $R^4$ to $R^6$ are identical or different $C_4$–$C_{30}$-alkyl, $C_7$–$C_{30}$-aralkyl or $C_{10}$–$C_{30}$-aryl radicals which optionally contain ether oxygen atoms, carbonyl groups, hydroxyl groups, alkoxy groups, carboxyl groups, cyano groups, carboxylic ester groups, sulfo groups, phosphonic acid groups, nitro groups, halogen atoms and/or unsubstituted or $C_1$–$C_4$-alkyl-substituted amino groups as functional groups, and $R^{11}$ to $R^{15}$ are, independently of one another, hydrogen or identical or different $C_1$–$C_{30}$-alkyl radicals, $C_7$–$C_{30}$-aralkyl radicals, $C_6$–$C_{30}$-aryl radicals, $C_1$–$C_{30}$-alkoxy groups, $C_7$–$C_{30}$-aralkoxy groups, $C_6$–$C_{30}$-aryloxy groups or dihydrocarbylamino groups having identical or different $C_1$–$C_{30}$-alkyl radicals, $C_7$–$C_{30}$-aralkyl radicals and/or $C_6$–$C_{30}$-aryl radicals as hydrocarbyl radicals which optionally contain ether oxygen atoms, carbonyl groups, hydroxyl groups, alkoxy groups, carboxyl groups, cyano groups, carboxylic ester groups, sulfo groups, phosphonic acid groups, nitro groups, halogen atoms and/or unsubstituted or $C_1$–$C_4$-alkyl-substituted amino groups as functional groups, where at least one of the radicals $R^{11}$ or $R^{15}$ has to be hydrogen, at least one of the radicals $R^{11}$ to $R^{15}$ being a long-chain linear or branched alkyl radical having at least 8 carbon atoms and the remaining radicals $R^{11}$ to $R^{15}$ are optionally linked in pairs to form rings, $L^2$ is an auxiliary ligand selected from the group consisting of oxo, halides, pseudohalides, carboxylates, phenoxides, alkoxides, enolates, ketones, ethers, amines, amides, urea, urea derivatives and water or a further ligand $L^1$ or a free coordination site, X is oxo oxygen or an unsubstituted or $C_1$–$C_4$-alkyl-substituted imido ligand, Z is phosphorous or arsenic, m is 1 or 2 and n is 1, 2 or 3.

2. A catalyst I as claimed in claim 1 in which M is molybdenum or tungsten.

3. A catalyst of the general formula Ia or Ib as claimed in claim 1

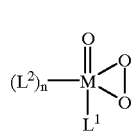

(Ia)

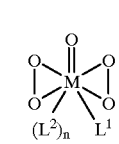

(Ib)

where
$L^2$ is water and the variables M, $L^1$ and n are as defined above.

4. A catalyst I as claimed in any of claim 1, where $L^1$ is an amine oxide ligand II bearing $C_1$–$C_{20}$-alkyl groups as radicals $R^1$ to $R^3$, where at least one of the radicals $R^1$ to $R^3$ has to be a $C_{12}$–$C_{20}$-alkyl group and the two other radicals can be linked to form a saturated 5- or 6-membered ring which can contain further hetero atoms selected from the group consisting of oxygen and nitrogen.

5. A catalyst I as claimed in claim 1 which $L^1$ is a phosphine oxide or arsine oxide ligand III bearing $C_4$–$C_{20}$-alkyl groups as radicals $R^4$ to $R^6$.

6. A process for preparing a catalyst I as claimed in claim 1 which comprises preparing the catalytically active complex of the general formula I from another complex of the metal M and hydrogen peroxide.

7. A process for preparing epoxides of the general formula IV

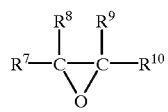

(IV)

where $R^7$ to $R^{10}$ are identical or different and are hydrogen or unsubstituted or substituted alkyl, alkenyl, heteroalkyl, cycloalkyl, aryl or heteroaryl radicals, where the radicals $R^7$ to $R^{10}$ can also be linked to form rings, or substituents based on elements of the 4th to 7th main group of the Periodic Table of the Elements, from olefins of the general formula V

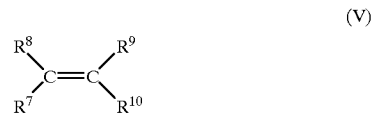

(V)

using aqueous hydrogen peroxide, wherein the epoxidation of the olefins V is carried out in the presence of a catalyst I as claimed in claim 1.

8. A process for preparing epoxides IV as claimed in claim 7, wherein the epoxidation of the olefins V is carried out using aqueous hydrogen peroxide in two liquid phases which are not completely miscible with one another.

9. A process for preparing propylene oxide from propene as claimed in claim 7.

10. A process for preparing vinyloxirane from 1,3-butadiene as claimed in claim 7.

* * * * *